US012097225B2

(12) United States Patent
Soman et al.

(10) Patent No.: US 12,097,225 B2
(45) Date of Patent: Sep. 24, 2024

(54) COMPOSITION FOR COMPETITIVE INHIBITION OF PATHOGENS AND RESTORATION OF MICROBIAL ECOLOGICAL BALANCE

(71) Applicant: Sanzyme Biologics Private Limited, Hyderabad (IN)

(72) Inventors: Raunak Jay Soman, Hyderabad (IN); Venkat Swamy Malisetty, Hyderabad (IN); Jay Soman, Hyderabad (IN)

(73) Assignee: Sanzyme Biologics Private Limited, Hyderabad (IN)

( * ) Notice: Subject to any disclaimer, the term of this patent is extended or adjusted under 35 U.S.C. 154(b) by 59 days.

(21) Appl. No.: 16/788,990

(22) Filed: Feb. 12, 2020

(65) Prior Publication Data

US 2020/0289585 A1 Sep. 17, 2020

(30) Foreign Application Priority Data

Feb. 12, 2019 (IN) ............................ 201941005414

(51) Int. Cl.

*A61K 35/742* (2015.01)
*A61K 31/192* (2006.01)
*A61K 31/194* (2006.01)
*A61P 15/02* (2006.01)
*A61P 31/04* (2006.01)

(52) U.S. Cl.

CPC .......... *A61K 35/742* (2013.01); *A61K 31/192* (2013.01); *A61K 31/194* (2013.01); *A61P 15/02* (2018.01); *A61P 31/04* (2018.01)

(58) Field of Classification Search

CPC .............................. A61P 15/02; A61K 35/742
See application file for complete search history.

(56) References Cited

FOREIGN PATENT DOCUMENTS

| | | | | |
|---|---|---|---|---|
| EP | 1263483 B1 * | 3/2007 | ......... | A61F 13/8405 |
| WO | WO-2006104564 A1 * | 10/2006 | ........... | A61K 31/192 |
| WO | WO2017/083549 A1 | 5/2017 | | |

OTHER PUBLICATIONS

Boris, et al.; "Adherence of Human Vaginal Lactobacilli to Vaginal Epithelial Cells and Interaction with Uropathogens"; Infection and Immunity; May 1998; 66:5 p. 1985-1989.

Cribby, et al.; "Vaginal Microbiota and the Use of Probiotics"; Interdisciplinary Perspectives on Infectious Diseases; vol. 2008; Article ID 256490; 9 pages; (2008).

Lee, et al.; "Probiotics prophylaxis in children with persistent primary vesicoureteral reflux"; Pediatric Nephrology; vol. 22; pp. 1315-1320 (2007). (Abstract Only).

Reid et al., "Oral probiotics can resolve urogenital infections"; FEMS Immunology and Medical Microbiology 30 (2001) 49-52.

Shalev et al.; "Ingestion of Yogurt Containing Lactobacillus acidophilus Compared With Pasteurized Yogurt as Prophylaxis for Recurrent Candidal Vaginitis and Bacterial Vaginosis"; Arch Fam Med.; 5:593-596 (1996).

Akbas MY, et al. "Use of organic acids for prevention and removal of Bacillus subtilis biofilms on food contact surfaces", Food Sci Technol Int. Oct. 2016;22(7):587-597; DOI: 10.1177/1082013216633545, 11 pages.

Akbas MY, "Effectiveness of Organic Acid Treatments for Inhibition and Removal of *E. coli* Biofilms", Hacettepe Journal of Biology and Chemistry, 2016, 44 (1): 35-45.

Liu, M et al., "The specific anti-biofilm effect of gallic acid on *Staphylococcus aureus* by regulating the expression of the ica operon", Food Control (2016), http://dx.doi.org/10.1016/j.foodcont.2016.09.015, 6 pages.

Shao D, et al. "Inhibition of Gallic Acid on the Growth and Biofilm Formation of *Escherichia coli* and *Streptococcus mutans*", J Food Sci. Jun. 2015;80(6):M1299-305.

"9: Kirby-Bauer (Antibiotic Sensitivity)" obtained from Libre Texts™ Biology at https://bio.libretexts.org/@go/page/3483 (accessed 2023, UC Davis Library, the California State University Affordable Learning Solutions Program), 4 pages.

Rao S, "Zone diameters of antimicrobial agents according to CLSI guidelines 2011" obtained from https://www.google.com/url?client=internal-element-cse&cx=002506909840376664814:qyoad8zfsws&q=https://www.microrao.com/micronotes/pg/kirby_bauer.pdf&sa=U&ved=2ahUKEwjOm4GG0aqBAxU6kokEHRVODnAQFnoECAMQAg&usg=AOvVaw3rnaJeIK-hJnJfs0ZA3Boy (dated Aug. 17, 2012), 13 pages.

* cited by examiner

*Primary Examiner* — Michelle F. Paguio Frising
*Assistant Examiner* — Grant C Currens
(74) *Attorney, Agent, or Firm* — Amin Wasserman Gurnani LLP; George M. Carrera, Jr.; Valerie Neymeyer-Tynkov

(57) ABSTRACT

Disclosed are compositions for competitive inhibition of pathogens against pathogenic infections comprising (a) *Bacillus coagulans*; (b) *Bacillus subtilis*; (c) citric acid; and (d) gallic acid including any combinations thereof. The compositions disclosed in this invention is capable to treat and prevent pathogenic infections of the genital organs as well as suitable for treatment and prevention of dermal infections. A method of preventing recurrence of the infections by way of supporting the growth of inherent natural doderlein microbial populations due to application of the compositions of the present invention are also disclosed. Further, use of the compositions of the present invention obviates the need of prior specific diagnosis of the infections due to its broad spectrum activity against multiple bacterial and fungal pathogens.

5 Claims, No Drawings

COMPOSITION FOR COMPETITIVE INHIBITION OF PATHOGENS AND RESTORATION OF MICROBIAL ECOLOGICAL BALANCE

This application claims priority to Indian Provisional application 201941005414, filed on Feb. 12, 2019, which is hereby incorporated by reference herein.

TECHNICAL FIELD

The present invention relates to the field of probiotic compositions. The present field of invention is also related to the treatment and prevention of microbial pathogens pertaining to the infection of the genital and reproductive system. The microbial pathogens included and intended to be treated are diverse aerobic and anaerobic bacterial pathogens of the human vagina. The present invention also includes within its scope the prevention and treatment of vaginal yeast infections through the probiotic compositions disclosed in this present invention.

BACKGROUND

The human vagina is a unique warm and moist chamber that is home to a considerable number of microbial population. A healthy adult female vaginal microflora includes several kinds of bacteria and yeast and other microbiota of lesser known species. The vaginal microbiome contains predominantly the lactic acid producing *Lactobacillus. Lactobacillus iners, Lactobacillus crispatus, Lactobacillus gasseri, Lactobacillus jenesenii*, followed by *Lactobacillus acidophilus, Lactobacillus bulgaricus, Lactobacillus rhamnosus, Lactobacillus leichmanni, Lactobacillus vaginalis, Lactobacillus plantarum, Lactobacillus casei* are some of the major *Lactobacillus* bacteria found in a healthy human vagina of pre-menopause age. This list is non-exhaustive in its nature. Other bacterial species those colonizes the human vagina might include other lactic acid producing bacterial species from the genera *Leptorichia, Leuconostoc, Atopobium, Streptococcus* instead of *Lactobacillus* but *Lactobacillus* remains to be the most common of all and the most preferred to retain a healthy state. It is well established that all ethnic populations of the world possess one or the other kind of lactic acid producing *Lactobacillus* predominant bacteria inside the vagina. Almost all of the vaginal miccrobiota found in the vaginal epithelium are gram positive in nature. Production of lactic acid inhibits various pathogenic invasions in the vagina. Lactic acid producing bacteria also produces hydrogen peroxide that inactivates deadly viruses such as Human Immunodeficiency Virus, Herpes Simplex virus, or other pathogenic bacteria like *Trichomoas vaginalis, Gardnerella vaginalis*, or other bacteria those responsible for bacterial vaginosis. There are of course other species of bacteria too, found in the vagina but there numbers are negligible. Lactic acid producing bacteria controls the over-growth of these other bacterial population and maintains the optimum count of different bacteria in the vagina. Production of lactic acid by *Lactobacillus* is responsible for maintaining a low acidic pH 4.5, preferably lesser, thereby discouraging other bacteria from thriving there thus acting as a natural barrier to unwanted microbial imbalances inside the vagina. The optimum vaginal pH ensures prevention of unwanted microbial flora such as yeast and different other bacteria other than *Lactobacillus*. In normal circumstances, a healthy human vagina is considered self sufficient to retain its healthy pH levels. The healthy *Lactobacillus* count is replenished automatically if supported by abundance of glycogen eventually broken down to complex sugars along with proper diet and a healthy lifestyle.

The natural microbial population of human vagina also includes a limited population of yeast cells in its native state. *Candida albicans*, typically a fungus is also a natural inhabitant of the vagina in negligible quantities. Although *C. albicans* is the only dominant species from the *Candida* genus that is found in the vagina, other common species include *C. glabrata, C. parapsilosis, C. tropicalis*, and *C. krusei*. It is opined that, vaginal yeast shares a commensal relationship with its host. Yet, sometimes *Candida* spp have also been termed as an endo-symbiont playing an indirect role in maintenance of a balanced vaginal microbial ecosystem. Being the natural inhabitants of the vaginal ecosystem, it is proposed to compete with other undesirable fungal invaders within the vagina at the first place. Therefore, a balanced population of vaginal bacterial and yeast cells is desirable however, it is also known that an increase in *Candida* albican population is responsible for vaginal yeast infections (vulvovaginitis) as well.

It is inherently a challenge to retain a natural balance of the vaginal microbial ecosystem. There is always a competition prevailing between the bacterial and the yeast population within the female genital system. Such an imbalance is obvious due to several direct or indirect factors. Hormonal imbalances resulting from excess stress in today's lifestyle in almost all adult females is one major reason of an imbalanced microbial population in their vagina. Stress also contributes in the imbalance of secretion of various female reproductive hormones. As such, a female undergoes fluctuations in hormones during her varying phases of menstrual cycle. For example, increases in estrogen levels are common prior to occurrence of menstrual bleeding. Such hormonal imbalance contributes in disturbing the natural balance of vaginal ecosystem. In addition, use of contraceptive devices, sexual intercourse, lifestyle disorders like diabetes, and use of various antibiotics ultimately have been shown to adversely affect the natural balance of a healthy vaginal microbiota predominantly affecting and reducing the count of healthy *Lactobacillus* from the vagina. This leads to various symptomatic or asymptomatic changes in the general course of life such as excessive vaginal discharge with a fishy odour called as leucorrhoea, vaginal itching, etc, that disturbs the general flow of life causing irritation and other associated social difficulties. These also may lead to severe pathogenic infections called as bacterial vaginosis, aerobic vaginitis as well as severe yeast or fungal infections, which are most of the times asymptomatic. Present technical research on this subject have also established that occurrence or presence of such pathogenic infections within the female reproductive system also increases the chances of contracting other severe sexually transmitted infections ranging from human immunodeficiency virus, hepatitis, human papillomavirus, *Neisseria gonorrhoeae, Chlamydia trachomatis* among others. Therefore, pathogenic infections of the vagina or other female genital tract of the vagina invites a huge risk in terms of contracting AIDS or cancer or other deadly sexually transmitted diseases. Hence, pathogenic infections of the human female genitalia are the doorstep of life-threatening diseases. An early detection, prevention and treatment of such pathogens is always necessary before it paves the way to such deadly diseases. Generally, treatment of vaginal pathogens has been performed with antibiotics such as metronidazole and clindamycin (for bacterial vaginosis), fluconazole, amphotericin-B (as antifungal) or others but it is an acknowledged fact that antibiotic treatment further contributes to the imbalance of inherent vaginal bacteria since antibiotics completely kills all kinds of bacteria present in the vagina including the lactic acid producing bacteria which is necessary for maintaining a good and healthy vaginal microbial ecosystem. The extensive use of antibiotics kills the probiotic *Lactobacillus* population of the vagina and sets an opportunity of overgrowth of vaginal yeast particularly and most commonly *Candida albicans*. An overgrowth of vaginal yeast is very common and undetectable. Increase in the vaginal yeast count is naturally reversible if proper caution is exercised. However, vaginal yeast infections (termed as Vaginal Candidiasys) demands treatment with antifungal drugs, which otherwise if left untreated impose serious medical complications provided the infections also enter the blood stream.

Chronic yeast infections of the vagina are also very common wherein the infection comes back even after treatment with antifungal drugs (fluconazole). Recurring yeast infections are caused due to several risk factors such as pregnancy, birth control pills or contraceptives, estrogen therapy, regular antibiotic use, diabetes and conditions that affect the immune system. Therefore, it becomes necessary to undergo treatment against recurring yeast infections repeatedly and multiple times which is devastating for a female of any given age. The problem of recurring yeast infection is more intense if caused by other *Candida* species, such as *C. glabrata*. Present antifungal treatment with a mycostatin vaginal creams, vaginal gels containing the antifungals amphotericin B and flucytosine might not be totally effective at all in case of other yeast infections. None of these treatments have been reported to offer a permanent solution to the recurrence of vaginal yeast infections. Therefore, vaginal yeast infections are a major concern for all women across the world particularly those who fall under the age group of 15-45. Furthermore, in vitro results suggests the use of alternative agents other than antifungal fluconazole when treating vulvovaginitis caused by non-*albicans* species (especially *C. glabrata* or *C. krusei*) as these non albican strains have been reportedly found to be not susceptible to fluconazole (Sandra S Richter et. al., *Antifungal Susceptibilities of Candida* Species *Causing Vulvovaginitis* and *Epidemiology of Recurrent Cases*, J Clin Microbiol. 2005 May; 43(5): 2155-2162). Availability of such alternative agents are scarce and not commercially available.

Referring to bacterial infections of the vagina, Bacterial vaginosis (BV) is the most commonly known and the most frequent vaginal infections characterized by an imbalanced vaginal flora due to deficiency of lactobacilli. Bacterial vaginosis affects about 15-50% of reproductive aged women globally. Symptoms of BV are existence of a thin, homogeneous discharge and a strong vaginal odour, however most women with BV are unaware that they are the victims of BV. BV has also been associated with significant gynaecologic and obstetric complications including pelvic inflammatory disease, endometritis, and post-operative infections including post-partum endometritis. Besides, women also become prone to pre-term delivery, miscarriage, and amniotic fluid infections and an increased susceptibility to Human Immunodeficiency Virus (HIV) as well. *Gardnerella vaginalis* is known to be the most commonly invading pathogen to cause BV among other such as *Atopobium vaginae, Bacteroides* spp, *Molbiluncus, Megasphera, Mycoplasma hominnis, Peptostreptococcus, Prevotella* being particularly prevalent as well. Other infections due to aerobic bacteria includes pathogenic strains of *E. coli, Enterococcus faecalis*, and *Staphylococcus saprophyticus, Staphylococcus aereus*, Group B *Streptococcus*. Aerobic pathogenic infections of the vagina is termed as Aerobic Vaginitis (AV) which is distinct from BV. A study of 2015 reports that aerobic vaginitis requires treatment based on microscopy findings and a combined local treatment with any of the following which may yield the best results: antibiotic (infectious component), steroids (inflammatory component), and/or estrogen (atrophy component) (Donders G G et. al., *Selecting anti-microbial treatment of aerobic vaginitis*, Curr Infect Dis Reports. 2015 May; 17(5):477). Unlike BV, AV does not respond well to metronidazole. Clindamycin is therefore considered to be a better choice against AV. Fluoroquinolones, such as ciprofloxacin and ofloxacin, have been used in treatment because they have little effect on the normal flora allowing for a rapid recovery from AV (Evelyn Kaambo et. al., *Vaginal Microbiomes Associated With Aerobic Vaginitis and Bacterial Vaginosis*, published online 2018 Mar. 26.doi: 10.3389/fpubh.2018.00078).

The presently known treatments of bacterial vaginosis in general, has been achieved with antibiotics such as metrinadazole, clindamycin etc or lactate gels. But, it is reported that 20% to 30% of women with BV relapse within 1-3 months following standard antibiotic treatment. Besides it is also widely accepted that antibiotics completely washes off natural *Lactobacillus* bacteria as well, thereby washing off or depleting the natural microflora along with the pathogens. This leaves and provides enough scope for all pathogenic microbes to dominate the vaginal epithelial lining once again before the natural lactobacilli are able to re-colonize the vagina naturally. Irregularities and non-completion of the entire medication schedule by the subjects increases the possibilities of re-colonization by the pathogens earlier than the local *Lactobacillus* as well. Additionally, there also lies possibilities of recurrence of the pathoges due to descent from the gut, sexual intercourse, and other susceptible factors. Therefore, investigations and studies has been already conducted to check BV through the application of probiotics that may be effective in improved treatment or prevention of BV. *L. Rhamnosus* GR-1 and *L. fermentum* B-54 has been studied as local vaginal instillations to reduce BV (G. Reid et. al., "*Instillation of Lactobacillus and stimulation of indigenous organisms to prevent recurrence of urinary tract infections*" Microecology and Therapy, vol. 23, pp. 32-45, 1995). Some of the other known probiotics to check BV is reported. *Lactobacillus acidophilus* which was found as effective as treatment with trimethoprim/sulfamethoxazole. (See, S. J. Lee et. al. "*Probiotics prophylaxis in children with persistent primary vesicoureteral reflux*", Pediatric Nephrology, vol. 22, no. 9, pp. 1315-1320, 2007). Another study involving oral probiotic delivery of combined compositions *L. rhamnosus* GR-1 and *L. Reuteri* RC-14 probiotic group delivered a lactobacilli dominated normal vaginal microbiota restored from a BV vaginal flora to 37% of the patients as compared to 13% of the placebo patients. However, a different strain of *L. Rhamnosus* GG was conclusively found to be ineffective in treating or preventing BV (G. Reid et. al., "*Oral probiotics can resolve urogenital infections*" FEMS Immunology & Medical Microbiology, vol. 30, no. 1, pp. 49-52, 2001). In another research involving combination of *Lactobacillus* gasseri 335 and *Lactobacillus brevis* in a vaginal tablet adversely affected the adhesion of *G. Vaginalis* and the count of pathogenic *G. Vaginalis* was also significantly reduced (S. Boris et. al., "*Adherence of human vaginal lactobacilli to vaginal epithelial cells and interactions with uropathogens*", Infection and Immunity, vol. 66, no. 5, pp. 1985-1989, 1994). A successful investigation was reported that would confront *Candida albicans* (yeast) and BV infections of the vagina through regular and periodic intake of probiotic yogurt containing *Lactobacillus acidophilus*, (E. Shalev et. al., "*Ingestion of yogurt containing Lactobacillus acidophilus compared with pasteurized yogurt as prophylaxis for recurrent candidal vaginitis and bacterial vaginosis*" Archives of Family Medicine, vol. 5, no. 10, pp. 593-596, 1996).

All the above studies have shown potentials of using primarily lactic acid producing *Lactobacillus* either singly or in combination with different *Lactobacillus* strains to treat BV. But, there are also evidence available wherein many other *Lactobacillus* strains has been found ineffective in treatment of BV. As per a review article on Vaginal Microbiota and the Use of Probiotics (Sarah Cribby et. al. Interdisciplinary Perspectives on Infectious Diseases, volume 2008, Article ID 256490), various other studies on treatment against bacterial vaginosis with various other probiotic lactobacilli *acidophilus* strains were found to be completely ineffective as well. A probiotic formulation of *L. fermentum, L. gasseri* and *L. rhamnosus* was not successful in treating bacterial vaginosis. Furthermore, there also remains very rare chances of developing endocardiditis and bacterimia caused by lactobacilli. The review by Sarah Cribby et. al. prescribes prior proper documented evidence of using a specific particular *Lactobacillus* strain to be coined as suitable probiotic to combat BV since the mode of action of *Lactobacillus* bacteria was found to be highly strain specific. It could be concluded that not all *Lactobacillus* bacteria could function as a suitable probiotic against BV.

Although lactobacilli are naturally occurring bacteria present within a woman's vagina, overgrowth of lactobacilli might be responsible for causing cytolytic vaginosis (also known as *Lactobacillus* overgrowth syndrome) that disrupts normal vaginal environment and becoming more acidic, excessive vaginal itching that irritates and causes inflammation of the vaginal walls, and the vulva, pain during urination and sexual intercourse and elevated vaginal discharge. Sometimes, excessive vaginal discharge symptoms is confused with either bacterial vaginosis or candidiasis. Cytolytic vaginosis is becoming more common in subjects with high glucose serum levels. Treatment of cytolytic vaginosis has been suggested with treatment of vaginal douche with sodium bicarbonate (Anupama Suresh et al., Indian J Sex Transm Dis AIDS. 2009 January-June; 30(1): 48-50).

Therefore, it is proposed that there exists a high risk of development of cytolytic vaginosis due to treatment of bacterial vaginosis conditions with only *Lactobacillus* strains because of overgrowth of lactobacilli in the vagina. This will lead to further complications, as in such cases, it would be mistakenly concluded to increase BV rather than identification of cytolytic vaginosis. In another aspect, since it is factually established that the specific lactobacilli resident in each individual and each different communities of the world is diverse, treatment with different external strains of lactobacilli which is not common or was not priorly existing in such subjects may be not functional. That is to say, a probability that a specific strain of lactobacilli acting as a probiotic in one particular group or individual against BV may not be applicable as a probiotic in a different individual or a different community. In other words, it is advisable to develop such probiotic formulations that would augment the naturally existing lactobacilli strain previously existing in the vagina of the specific subject (called as doderlein vaginal microflora), rather than supplying a different other strains of external *Lactobacillus* through other *Lactobacillus* based probiotic formulation(s). This would also have the advantage of avoiding the risk of developing cytolytic vaginosis also, since such probiotic formulation would intentionally does not include any lactobacilli strain yet act as a biological catalyst to restore natural *Lactobacillus* microflora in the human vagina.

Additionally it is the need of the hour to develop a single probiotic formulation that would treat and prevent aerobic vaginitis and as well as bacterial vaginosis along with simultaneous vaginal yeast infections as well with a broad spectrum application against any and all *Candida* species other than *Canidida albicans*. Such a new probiotic formulation would also avoid undergoing prior separate and specific diagnostic steps to identify the nature of vaginal infections thereby decreasing the cost of expense, and time of recovery beyond any doubt.

US2006/0217443A1 publishes use of gallic acid in a pharmaceutical formulation that is capable of inhibiting *Triichomonas vaginalis, Gardnerella vaginalis*, and *Candida albicans* but not inhibiting the growth of *Lactobacillus acidophillus* with potential to treat or prevent vaginal infections caused by these three selective organisms. However, there is no evidence provided in this patent application that gallic acid although not inhibiting the growth of *Lactobacillus acidophilus* is capable of promoting the growth of lactic acid bacteria. Furthermore, the effect of gallic acid alone on other species of *Lactobacillus* bacteria remains unknown. It is also not provided that gallic acid would inhibit the diverse microbial pathogens responsible for bacterial vaginosis as detailed above. Likewise, only gallic acid would be unable to treat or prevent aerobic vaginitis pathogens and different *candida* species.

WO2017/083549 further discloses a probiotic delivery system as a vaginal suppository composition comprising a pharmaceutically acceptable matrix that is solid at room temperature and in a dry environment but melts when comes in contact with the inner mucosa of the rectum or the vagina wherein the said matrix comprises a mixture of fatty acids selected from sodium bicarbonate, citric acid, Vitamin C, lauric acid, coconut oil, shea butter, and other pharmaceutically acceptable items such as polyehylene glycol, hydrogels, cocoa butter, glycerinated gelatin, mineral oil, or shark liver oil. The composition of WO2017/083549 also includes one or more species of probiotic bacteria, and a pH stabilizing agent. The probiotic bacteria experimentally presented in the delivery system of this patent publication are *L. acidophilus* DDS 1, *Bifidobacterium lactis, L. plantarum* WCFS1, *L. casei* GG, *L. rhamnosus* GG, *L. brevis, Bifidobacterium longum, L. salivarius, Streptococcus thermophilus, Bifidobacterium bifidum*. Other theoretically disclosed probiotic bacteria that could be possibly included in this vaginal suppository are *L. planetrium, L. Casei, Bifidobacterium longum, L. lactis, Bacillus coagulans, L. Bulgaricus*, and *L. gasseri*. The suppository composition also includes a bunch of prebiotics and pH solubilizing agent(s) although no proper experimental details has been disclosed in this particular patent disclosure. There is no evidence of treatment against pathogenic infections of the vagina at all in this patent publication. Furthermore, there is lack of enablement of actual technical details, since combination of so many bacteria are also prone to experience inter-bacterial interference and competition. Therefore, such a formulation with so many bacterial types is not practically suggested.

Another patent publication US2018/0250318 discloses a composition particularly useful in maintaining and supporting healthy microflora in the female urogenital tract comprising a first therapeutic agent and a second therapeutic agent wherein the first therapeutic agent is a pentose or a disaccharide and the second therapeutic agent is an organic acid or selected from cyclodextrin, or a pectic substance or a non-digestible polysaccharide. Similar to the above prior arts, experimental details of actual treatment of vaginal infections including AV, BV and yeast infections are missing in this particular reference as well.

Thus, a review of the current state of the art lacks a proper probiotic measure to treat diverse pathogenic infections of the vagina. It would be highly appreciated to provide a single beneficial probiotic formulation that will be able to treat any kind of vaginal pathogens including a variety of pathogens causing bacterial vaginosis, or aerobic vaginitis, as well as different yeast infections of the vagina. Another definite advantage is such a formulation will prevent from further aggravating of the infections due to the delay caused in diagnosis. Such a formulation is desirable because this would avoid the delay of treatment and additional diagnostic measures to identify the specific nature of treatment on a particular subject thereby also decreasing the total cost of treatment as well. Hence, such a formulation would be easily affordable by the subjects who are more prone to vaginal infections due to sexual intercourse with multiple partners or genital exposure related to their profession. The present invention discloses a unique probiotic composition that successfully addresses the present drawbacks of all the existing methods of treatment against all known bacterial or yeast infections of the human female genital system ranging from vagina, or the anus, rectum and the like.

OBJECTIVES OF THE PRESENT INVENTION

One objective of the present invention is to replenish the natural vaginal microflora through the use of new probiotic compositions of the present invention.

Another objective of the present invention is to promote the growth of local lactobacilli inside the vagina of a respective subject through the use of new probiotic compositions that does not include an external source of *Lactobacillus.*

A further objective of the present invention is to provide a new probiotic composition for the treatment of bacterial vaginosis due to any and almost all known types of bacterial or fungal pathogens or any other infectious microorganism.

Another objective of the present invention is provide a new probiotic composition that is capable to prevent and treat aerobic bacterial infections of the vagina causing aerobic vaginitis as well.

One more objective of the present invention is to overcome the present drawbacks, side effects or limitations of treatment of vaginal yeast infections including those caused by either *Candida albicans* as well as all other known types of pathogenic yeast or fungal species of the vagina.

One further objective of the present invention also includes the prevention and treatment of any and all bacterial infections such as bacterial vaginosis, aerobic vaginitis and yeast or fungal infections without the need of specific prior diagnosis of the nature of the vaginal infection.

One further objective of the present invention also includes the prevention and treatment of recurrent vaginal bacterial infections such as bacterial vaginosis, aerobic vaginitis and yeast or fungal infections.

The basic objective of the invention is to retain consistent healthy vaginal pH of between 3.5-4.5 that promotes healthy microbiota of the human vagina or any other genital or reproductive parts of the human female such as rectum or the anus or the inner endometrial microflora through administration of the probiotic compositions of the present invention.

It is also an objective of the present invention to enable and maintain a healthy balance of the human female reproductive system irrespective of intrinsic and extrinsic disturbances caused due to hormonal imbalances, mood swings, different other medications or antibiotic treatment, vaginal douches, menstrual cycles, sexual intercourse, multiple sexual partners etc (non-exhaustive) with the probiotic compositions of the present invention.

SUMMARY

According to one embodiment of the invention, isolation of the infected vaginal swabs from different subjects followed by identification diverse bacterial and fungal pathogens infecting the human vagina is provided.

According to another embodiment of the invention, various formulations at different concentrations that includes the present composition of the present invention comprising *Bacillus coagulans, Bacillus subtilis*, citric acid and gallic acid are provided.

According to one more embodiment of the invention, the extent of protection measured in terms of zone of inhibitions obtained by various formulations at different concentrations that includes the present composition of the present invention comprising *Bacillus coagulans, Bacillus subtilis*, citric acid and gallic acid against the isolated vaginal pathogens are provided.

According to another embodiment of the invention, comparative growth of *Bacillus coagulans* and *Bacillus subtilis* in presence of the composition of the present invention have been provided.

According to yet another embodiment of the invention, comparative growth of inherent doderlein *Lactobacillus* species of the human vagina in presence of is also provided.

According to further embodiment of the invention, mechanism of action of the composition of the present invention is provided.

According to yet another embodiment of the invention, a composition comprising *Bacillus coagulans, Bacillus subtilis*, citric acid, gallic acid in the presence of excipients selected from bioadhesives, disintegrating agents, binders, humectants, anticaking agents, foaming agents diluents and carriers is also disclosed, wherein the bioadhesive is selected from carbomers, carbopol, polycarbophil, disintegrating agents are selected from beta-cyclodextrin, sodium bicarbonate, adipic acid, boric acid, sodium glycolate, binders are selected from starch and disaccharides, poly vinyl pyrollidone, humectant is selected from glycerine, aloevera, the anticaking agent selected from silicon dioxide, sodium bicarbonate, and adipic acid. The list of excipients provided are in no-way limiting the scope of the present invention and is non-exhaustive in nature.

The invention is further described in terms of the non-limiting examples as provided herein below. A person skilled in the art would appreciate that any modifications or alterations of the invention as described herein below are to be construed well within its scope and ambit of the invention.

An embodiment of the invention discloses a composition for competitive inhibition of pathogens against but not limited to bacterial vaginosis, aerobic vaginitis, vaginal yeast and fungal pathogenic infections without the need of prior diagnosis thereof and restoration of microbial ecological balance comprising: (a) *Bacillus coagulans*; (b) *Bacillus subtilis*; (c) citric acid; and (d) gallic acid, including any combinations thereof.

An embodiment of the invention discloses a composition comprising *Bacillus coagulans* and *Bacillus subtilis* including any combinations thereof.

An embodiment of the invention discloses a composition comprising *Bacillus coagulans*, citric acid, and gallic acid including any combinations thereof.

An embodiment of the invention discloses a composition comprising *Bacillus subtilis*, citric acid, and gallic acid including any combinations thereof.

An embodiment of the invention discloses a composition wherein *Bacillus coagulans* is present at a concentration of up to 1 billion colony forming units (cfu), and *Bacillus subtilis* is present at a concentration of up to 1 billion colony forming units (cfu), citric acid between 10 mg to 100 mg and gallic acid between 10 mg to 100 mg per unit dose.

An embodiment of the invention discloses a composition wherein *Bacillus coagulans* is present at a concentration of 250 million cfu to 550 million cfu, preferably between 350 million cfu to 550 million cfu; *Bacillus subtilis* is present at a concentration of 250 million cfu to 550 million cfu, preferably between 350 million cfu to 550 million cfu; citric acid between 10 to 50 mg and gallic acid between 10 to 50 mg per unit dose.

An embodiment of the invention discloses a composition further including *Bacillus laterosporus* up to 1 billion colony forming units (cfu) per unit dose.

An embodiment of the invention discloses a composition further comprising excipients selected from bioadhesives, disintegrating agents, binders, humectants, anticaking agents, foaming agents diluents and carriers.

An embodiment of the invention discloses a composition wherein the bioadhesive is selected from carbomers, carbopol, polycarbophil, disintegrating agents are selected from beta-cyclodextrin, sodium bicarbonate, adipic acid, boric acid, sodium glycolate, binders are selected from starch and disaccharides, poly vinyl pyrollidone, humectant is selected from glycerine, aloevera, the anticaking agent selected from silicon dioxide, sodium bicarbonate, and adipic acid.

An embodiment of the invention discloses a composition provided in any of the form selected from a gel, ointment, cream, tablet, capsule, pessary, foam, washes, tampons, applicators, pads, for use as oral, or topical, or any site-specific mode of application.

An embodiment of the invention discloses a composition wherein *Bacillus coagulans* and *Bacillus subtilis* is present in the form of spores which germinates into vegetative forms as soon as contacted with the internal vaginal environment or the dermis optionally aided by the presence of citric acid and gallic acid.

An embodiment of the invention discloses a composition is stable for at least 2 years at temperatures up to 40° C. in absence of cold chain storage conditions.

An embodiment of the invention discloses a composition a method of competitive inhibition of pathogens and restoration of inherent doderlein bacteria without administering any *Lactobacillus* bacteria from external sources thereby maintaining microbial ecological balance of the reproductive and genital organs particularly the vagina for treatment of bacterial vaginosis, aerobic vaginitis, vaginal yeast and fungal pathogenic infections without the need of prior diagnosis thereof using a composition comprising (a) *Bacillus coagulans*; (b) *Bacillus subtilis*; (c) citric acid; and (d) gallic acid, including any combinations thereof, further wherein *Bacillus coagulans* and *Bacillus subtilis* is present at a concentration up to 1 billion cfu in the form of spores, citric acid between 10 mg to 100 mg and gallic acid between 10 mg to 100 mg per unit dose.

An embodiment of the invention discloses a method of prevention and reduction of recurrence of pathogenic infections using a composition comprising (a) *Bacillus coagulans*; (b) *Bacillus subtilis*; (c) citric acid; and (d) gallic acid, including any combinations thereof, further wherein the growth of doderlein *Lactobacillus* bacteria in the presence of *Bacillus coagulans* and *Bacillus subtilis* is more than the growth of doderlein *Lactobacillus* bacteria without the presence of *Bacillus coagulans* and *Bacillus subtilis.*

DETAILED DESCRIPTION

As enumerated above, unlike the other probiotic compositions provided in the prior art including a *Lactobacillus* bacteria, the present invention does not include any *Lactobacillus* bacteria at all. The present probiotic composition includes particularly *Bacillus coagulans* and *Bacillus subtilis*. Presence of *Bacillus coagulans* produce and release lactic acid, which in turn promotes the growth of other *Lactobacillus* bacteria to thrive and multiply their counts exponentially. Therefore it acts as an in-situ producer of lactic acid thereby preventing growth of pathogenic *E. coli* and *Streptococcus* strains within the vagina, Furthermore, *Bacillus cogaulans* and *Bacillus subtilits* are bacteria which are already recognized to be probiotics of the digestive system, and imposes no serious health risks to be administered in the human reproductive system as well. *Bacillus coaglauns* and *Bacillus subtilis* also act by producing effective bacteriocins that kill wide ambit of pathogenic bacteria causing bacterial vaginosis. At the same time, the probiotic composition as a whole also bears the potential to combat other aerobic vaginitis causing microbes and vaginal yeasts including *Candida albicans* including other fungal pathogens other than *C. albicans* as well. The probiotic composition of the present invention therefore is a major technical development in the domain of treatment of all kinds of female genital infections and hence avoids the requirement of specific prior diagnosis. The probiotic composition of the present invention is therefore advantageous and acts in a synergistic manner to address multiple requirements in a single formulation which are currently absent in the present state of the art. The probiotic composition of the present invention is capable to be formulated as a vaginal suppository to be directly instilled internally within the vagina with or without the help of a vaginal applicator. Alternatively, the probiotic composition of the present invention is capable to be formulated as a composition for oral administration which traverses down the digestive tract to finally settle in the internal genital environment. The probiotic composition of the present invention can also be administered as a vaginal douche or any genital cleansing formulations or a tampon, sanitary pads and napkins or the like.

The invention is further described in the non-limiting working examples as described below.

Example 1

Isolation of Infectious Strains from the Human Vagina

I. Collection for Vaginal Swab Specimens: HiCulture™ Transport Swabs were used for collection of specimens. Carefully swab was inserted into vagina about 2 inches (5 cm) past the introitus and gently rotated the swab for 10 to 30 seconds. It was made sure that the swab touches the vagina walls so that moisture is absorbed by the swab and then swab was withdrawn without touching the skin. The capped swab with the sample was inserted till the bottom of the sample collection tube containing medium and the tube was capped firmly. All such specimens collected from a few subjects in the form of swabs obtained from the vagina of the said subjects were labeled and transported to the laboratory in a temperature controlled box. After the transportation, the specimens were inoculated in appropriate medium as soon as possible.

II. Enrichment of Specimens: The collected swabs were inoculated into Soybean Casein Digest Medium (SCDM) and Potato Dextrose medium (PDB). The mediums were kept under incubation at 37° C. for 24-48 hrs. Enrichment in SCDM and PDB enumerate the presence of bacteria and fungi/yeast respectively.

III. Isolation of vaginal pathogens: After incubation, 1 ml of enriched broth of SCDM and PDB were inoculated into sterile petri plate and then poured SCDA (Soyabean Casein Digest Agar) and PDA (Potato Dextrose Agar) in respective plates. After solidification of agar, plates were incubated at 37° C. for 24-72 hrs. Uninnoculated control plates were kept for incubation along with inoculated plates to ensure sterility of media and plate preparation.

Once the incubation was over, plates were observed for different colony morphology and growth pattern. All the different colonies were identified from SCDA and PDA plate. Every isolated colony were re-streak on earlier prepared and pre-incubated sterile SCDA and PDA plates. Each colony was streak on single plate. All plates of SCDA are kept for incubation at 37° C. and PDA at 30° C. for 24-72 hrs.

Example 2

Identification of Isolated Pathogens

All the colony morphology was recorded as per Bergey's manual of bacteriology and staining were performed for isolates. Three different fungal pathogens (identified as VP01, VP02, VP06) and three different bacterial pathogens (identified as VP03, VP04 and VP05) which was most commonly found to occur from the infectious swabs were individually cultured for further examination as detailed below.

Example 3

Formulation of Anti-Vaginitis Probiotic Composition

Antimicrobial activities against isolated vaginal pathogens (i.e. VP01, VP02, VP06, VP03, VP04 and VP05) were individually screened and analyzed to conclude and find effective probiotic compositions.

Example 3.1

Different combination of selected probiotics strains with variation in potency were formed and underwent potential antimicrobial effect against isolated vaginal bacterial and fungal pathogens. The extents of zone of inhibition in antimicrobial activity were considered for selection of formulation. The table 1 below describes the working of the invention. The probiotic compositions of the present invention comprises (a) *Bacillus coagulans* (B.C); (b) *Bacillus subtilis* (B.S); (c) citric acid (CA); (d) gallic acid (GA); (e) beta-cyclodextrin (adhesive); (f) allentoin and (g) a pH regulator (h) lanolin (i) polyethylene glycol (j) a cooling agent etc (k) a bioadhesive.

All the embodiments of the present invention and the working examples disclosed herein were conducted with *Bacillus coagulans* strain designated as SNZ1969 and *Bacillus subtilis* strain designated as SNZ1972. *Bacillus coagulans* SNZ1969 was deposited on Dec. 6, 2012 with Microbial Type Culture Collection & Gene Bank, Institute of Microbial Technology (A Constituent Establishment of CSIR), Sector 39-A, Chandigarh, India 160 036, with number assigned as Accession Number MTCC-5724. *Bacillus subtilis* SNZ1972 was deposited on Mar. 13, 2015 with Microbial Type Culture Collection & Gene Bank, CSIR-Institute of Microbial Technology, Sector 39-A, Chandigarh, India 160 036, with number assigned as Accession Number MTCC-5981. Although the experiments have been conducted with *Bacillus coagulans* SNZ1969 and *Bacillus subtilis* SNZ1972, the efficacy of the compositions of the present invention is not confined to these specific strains of *Bacillus coagulans* and *Bacillus subtilis*. The present invention is also capable to inhibit pathogenic infections and restore inherent doderlein bacteria comprising any given strain of *Bacillus coagulans* and *Bacillus subtilis*.

TABLE 1

| | | ZONE OF INHIBITION (in mm) | | | | | |
|---|---|---|---|---|---|---|---|
| SL | | Fungal Pathogens | | | Bacterial Pathogens | | |
| No. | Formulation | VP01 | VP02 | VP06 | VP03 | VP04 | VP05 |
| 1 | Gallic Acid (GA) | 35 | 35 | 9 | n-i | 9 | 11 |
| 2 | Citric Acid (CA) | 41 | 30 | n-i | 10 | 11 | 19 |
| 3 | GA + CA | 35 | 38 | 15 | 13 | 15 | 22 |
| 4 | BS* + GA + CA | 44 | 39 | 22 | 18 | 19 | 21 |
| 5 | Clotrimazole (commercial formulation) | n-i | 9 | 17 | n-i | 8 | n-i |
| 6 | A* | 45 | 39 | 19 | 13 | 11 | 16 |
| 7 | B* | 43 | 38 | 17 | 16 | 19 | 19 |
| 8 | C* | 42 | 34 | 21 | 18 | 21 | 21 |
| 9 | D* | n-i | n-i | 20 | 9 | 8 | 11 |
| 10 | *Bacillus subtilis* (1 billion spores) | — | — | 40 | — | — | — |
| 11 | *Bacillus coagulans* (1 billion spores) | — | — | 26 | — | — | — |
| 12 | *Bacillus laterosporus* (1 billion spores) | — | — | 22 | — | — | — |

Table 1 shows Initial Zone of Inhibition studies with various probiotic formulations.

A* is formulation that includes *Bacillus subtilis* (350 million spores), *Bacillus coagulans* (350 millison spores), Gallic acid (GA)(50 mg) and Citric Acid (CA)(25 mg) and *Bacillus laterosporus* (350 million spores). B* is a formulation that included *Bacillus subtilis* (350 million spores), *Bacillus coagulans* (350 million spores), GA (50 mg) and CA (25 mg). C* is formulation that include *Bacillus subtilis* (350 million spores), *Bacillus coagulans* (700 million spores), GA (50 mg) and CA (25 mg). Similarly D* is formulation that included *Bacillus coagulans* (100 million spores) along with GA (50 mg), CA (25 mg) along with Boric Acid. VP01, VP02 and VP06 are suspected fungal pathogens determined on the basis of morphological characteristics. VP03, VP04 and VP05 are suspected bacterial pathogens determined on the basis of morphological characteristics. The term 'n-i' denotes that there was no zone of inhibition obtained against the particular pathogen at all in presence of our probiotic formulations or the individual components thereof. The places left blank in the above table means that no experiment on those parameters were conducted at all.

Example 3.2

Based on the initial experiments above, various new formulations at different concentrations of each of the components were prepared and the corresponding zone of inhibition studies were performed. The zones of inhibition were also examined for each individual components at the same concentration levels as present in the respective combined formulations.

The various ranges of concentrations of each component of the invention is disclosed in the Table 2 below.

TABLE 2

| Serial No. | *B. coagulans* (million) | *B. subtilis* (million) | Citric Acid (mg) | Gallic Acid (mg) |
|---|---|---|---|---|
| 1. | 700 | 25 | 10 | 100 |
| 2. | 550 | 125 | 20 | 60 |
| 3. | 350 | 350 | 20 | 40 |
| 4. | 125 | 550 | 60 | 20 |
| 5. | 25 | 700 | 100 | 10 |

Table 2 shows Various Concentration Ranges of the Individual Components.

The various formulations made with the above mentioned different concentration ranges of the components mentioned in Table 2, is presented in Table 3 below.

TABLE 3

| Formulations | A | B | C | D | E |
|---|---|---|---|---|---|
| *B. cogulans* (in million) per unit dose | 700 | 550 | 350 | 125 | 25 |
| *B. subtilis* (in million) per unit dose | 25 | 125 | 350 | 550 | 700 |
| Citric Acid (in mg) per unit dose | 10 | 20 | 20 | 60 | 100 |
| Gallic Acid (in mg) per unit dose | 100 | 60 | 40 | 20 | 10 |

Table 3 shows Various Formulations prepared with each of the components at respective combination of concentration ranges.

The Zone of Inhibition were checked with the formulation A of Table 3, along with corresponding individual concentrations against each of the isolated pathogens VP01, VP02, VP06, VP03, VP04 and VP05 presented in Table 4 below.

TABLE 4

| Formulation (B.c & B.s in million, | ZONE OF INHIBITION (in mm) | | | | | |
|---|---|---|---|---|---|---|
| CA & GA in mg) | VP01 | VP02 | VP06 | VP03 | VP04 | VP05 |
| A [B.c (700) + B.s (25) + CA (10) + GA (100)] | 11 | 13 | 19 | 15 | 15 | 15 |
| *B. coagulans* (700) | n-i | 25 | n-i | 7 | 9 | 10 |
| *B. subtilis* (25) | 12 | 13 | 16 | n-i | 9 | 11 |
| CA (10) | n-i | n-i | n-i | n-i | n-i | n-i |
| GA (100) | 19 | 16 | n-i | 8 | 10 | 7 |

Table 4 shows Zone of Inhibition for Formulation A against individual components at the same concentrations thereof.

From the above Table 4, it is to be noted that in case of VP06, none of the components except *Bacillus subtilis* could inhibit VP06 but the combined formulation A shows greater extent (19 mm) of protection against VP06, as against only *Bacillus subtilis* (16 mm). Similarly, as against VP03 *Bacillus subtilis* and Citric Acid is unable to cause any inhibitory effect and *Bacillus coagulans* and Gallic acid shows negligible zone of inhibitions (7 & 8 respectively). Yet, the formulation shows substantial increase in the magnitude of zone of inhibition (15). Increase in the zone of inhibition is found to be subsistent as against VP06, VP03, VP04 and VP05 while acted by the combined formulation as against in presence of individual components.

The Zone of Inhibition were checked with the formulation B of Table 3, along with corresponding individual concentrations against each of the isolated pathogens VP01, VP02, VP06, VP03, VP04 and VP05 presented in Table 5 below.

TABLE 5

| Formulation (B.c & B.s in million, | ZONE OF INHIBITION (in mm) | | | | | |
|---|---|---|---|---|---|---|
| CA & GA in mg) | VP01 | VP02 | VP06 | VP03 | VP04 | VP05 |
| B [B.c (550) + B.s (125) + CA (20) + GA (60)] | 14 | 16 | 25 | 16 | 16 | 14 |
| *B. coagulans* (550) | n-i | 28 | n-i | 7 | 8 | 9 |
| *B. subtilis* (125) | 13 | 14 | 24 | n-i | 11 | 11 |
| CA (20) | n-i | n-i | n-i | 7 | n-i | n-i |
| GA (60) | 17 | 15 | n-i | 5 | 10 | 7 |

Table 5 shows Zone of Inhibition for Formulation B against individual components at the same concentrations thereof.

From the above Table 5, it is to be noted that in case of VP06, none of the components except *Bacillus subtilis* could inhibit VP06 but the combined formulation B shows increase (25 mm) of protection against VP06, as against only *Bacillus subtilis* (24 mm). The formulation shows substantial increase in the magnitude of zone of inhibition in case of VP03, VP04 and VP05 as against the zone of inhibition caused by the individual components. Increase in the zone of inhibition is found to be subsistent as against VP06, VP03, VP04 and VP05 while acted by the combined formulation as against in presence of individual components.

The Zone of Inhibition were checked with the formulation C of Table 3, along with corresponding individual concentrations against each of the isolated pathogens VP01, VP02, VP06, VP03, VP04 and VP05 presented in Table 6 below.

TABLE 6

| Formulation (B.c & B.s in million, | ZONE OF INHIBITION (in mm) | | | | | |
|---|---|---|---|---|---|---|
| CA & GA in mg) | VP01 | VP02 | VP06 | VP03 | VP04 | VP05 |
| C [B.c (350) + B.s (350) + CA (20) + GA (40)] | 16 | 17 | 23 | 17 | 17 | 15 |
| *B. coagulans* (350) | n-i | 17 | n-i | 6 | 8 | n-i |
| *B. subtilis* (350) | 13 | 13 | 26 | 8 | 13 | 12 |
| CA (20) | 23 | n-i | n-i | 8 | 10 | 8 |
| GA (40) | 16 | 15 | n-i | 7 | 9 | 6 |

Table 6 shows Zone of Inhibition for Formulation C against individual components at the same concentrations thereof.

From the above Table 6, the formulation shows substantial increase in the magnitude of zone of inhibition in case of VP03 (17), VP04 (17) and VP05 (15) as against the negligible zone of inhibition caused by the individual components. Increase in the zone of inhibition is found to be subsistent as against VP02, VP03, VP04 and VP05 while acted by the combined formulation as against in presence of individual components.

The Zone of Inhibition were checked with the formulation D of Table 3, along with corresponding individual concentrations against each of the isolated pathogens VP01, VP02, VP06, VP03, VP04 and VP05 presented in Table 7 below.

TABLE 7

| Formulation (B.c & B.s in million, CA & GA in mg) | ZONE OF INHIBITION (in mm) | | | | | |
|---|---|---|---|---|---|---|
| | VP01 | VP02 | VP06 | VP03 | VP04 | VP05 |
| D [B.c (125) + B.s (550) + CA (60) + GA (20)] | 21 | 20 | 25 | 17 | 14 | 12 |
| *B. coagulans* (125) | n-i | 13 | n-i | 5 | 7 | n-i |
| *B. subtilis* (550) | 12 | 12 | 26 | 9 | 12 | 12 |
| CA (60) | 22 | n-i | n-i | n-i | 10 | 8 |
| GA (20) | 16 | 18 | N-i | n-i | 9 | 6 |

Table 7 shows Zone of Inhibition for Formulation D against individual components at the same concentrations thereof.

Especially in the case of above formulation D shown above, the magnitude of protection obtained individually by *Bacillus coagulans* (5) and *Bacillus subtilis* (9) against VP03 are minimal. The individual components Citric acid and Gallic Acid is not active against VP03 at all. However, there is a substantial increase in the protection obtained in case of the combined formulation D (17 mm). Thus, there is substantial increase obtained by the combined formulation as against each of the components when present individually. Increase in the zone of inhibition is found to be subsistent as against VP02, VP03 and VP04 while acted by the combined formulation as against in presence of individual components.

The Zone of Inhibition were checked with the formulation E of Table 3, along with corresponding individual concentrations against each of the isolated pathogens VP01, VP02, VP06, VP03, VP04 and VP05 presented in Table 8 below.

TABLE 8

| Formulation (B.c & B.s in million, CA & GA in mg) | ZONE OF INHIBITION (in mm) | | | | | |
|---|---|---|---|---|---|---|
| | VP01 | VP02 | VP06 | VP03 | VP04 | VP05 |
| E [B.c (25) + B.s (700) + CA (100) + GA (10)] | 22 | 22 | 27 | 15 | 15 | 13 |
| *B. coagulans* (25) | n-i | 13 | n-i | 6 | 7 | 6 |
| *B. subtilis* (700) | 13 | 13 | 27 | 9 | 13 | 13 |
| CA (100) | 25 | n-i | n-i | 9 | 11 | 10 |
| GA (10) | 13 | n-i | n-i | n-i | 7 | 6 |

Table 8 shows Zone of Inhibition for Formulation E against individual components at the same concentrations thereof.

In the case of above formulation E shown above, the magnitude of protection obtained individually by *Bacillus coagulans* (13) and *Bacillus subtilis* (13) against VP02 are minimal. The individual components Citric acid and Gallic Acid is not active against VP02 at all. However, there is a substantial increase in the protection obtained in case of the combined formulation E (22 mm). Thus, there is substantial increase obtained by the combined formulation as against each of the components when present individually. Increase in the zone of inhibition is found to be subsistent as against VP02, VP03 and VP04 while acted by the combined formulation as against in presence of individual components.

The Zone of Inhibition were checked with all the formulations A to C of Table 3, against each of the isolated pathogens VP01, VP02, VP06, VP03, VP04 and VP05 is presented in Table 9 below.

TABLE 9

| Formulations (B.c & B.s in million, CA & GA in mg) | ZONE OF INHIBITION (in mm) | | | | | |
|---|---|---|---|---|---|---|
| | VP01 | VP02 | VP06 | VP03 | VP04 | VP05 |
| A [B.c (700) + B.s (25) + CA (10) + GA (100)] | 11 | 13 | 19 | 15 | 15 | 15 |
| B [B.c (550) + B.s (125) + CA (20) + GA (60)] | 14 | 16 | 25 | 16 | 16 | 14 |
| C [B.c (350) + B.s (350) + CA (20) + GA (40)] | 16 | 17 | 23 | 17 | 17 | 15 |
| D [B.c (125) + B.s (550) + CA (60) + GA (20)] | 21 | 20 | 25 | 17 | 14 | 12 |
| E [B.c (25) + B.s (700) + CA (100) + GA (10)] | 22 | 22 | 27 | 15 | 15 | 13 |

Table 9 shows Zone of Inhibition of all the Formulations A to E against VP01 to VP06 pathogens.

The present formulation with *Bacillus subtilis, Bacillus coagulans*, Gallic Acid and Citric Acid kills all the different infectious pathogens VP01 to VP06. However, the presently available commercial formulations could merely kill only selective pathogens. *Bacillus subtilis* has also shown wide spectrum activity especially against different fungal pathogens. Although different combinations containing *Bacillus subtilis*, gallic acid, and citric acid does show fair amount of broad-spectrum activity against most of the pathogens, presence of only these three components (i.e. *Bacillus subtilis*, gallic acid, and lactic acid) lacks continuous supply of lactic acid inside the vagina once the initial content of these three components are exhausted. *Bacillus coagulans* produces lactic acid and therefore continues to increase or replenish the vaginal microbial population with the native doderlein *Lactobacillus* species of the specific subject. This is phenomenal in also preventing the recurrence of the vaginal infectious pathogens in the long run. This is also explained in the following examples.

Example 4

Growth Profile of *Bacillus coagulans* and *Bacillus subtilis* in vaginal formulation at various pH greater than pH 7.

The pH of an infected vagina tends to be alkaline somewhere between pH 7-10. These experiments show that, within a span of 6 hours after exposure of the composition in contact of internal vaginal environment the pH comes down to pH 5-6 thereby turning the pH to acidic, and suitable to grow *Bacillus coagulans* and *Bacillus subtilis*, followed by Doderlein Bacteria.

Each of *Bacillus subtilis* (BS) and *Bacillus coagulans* (BC) present initially each at 350 million spores and the vaginitis formulation (VF) of the present invention comprising *Bacillus subtilis* (350 million spores) and *Bacillus cogulans* (350 million spores), along with citric acid and gallic acid were supplied with the following medium for measuring the growth of the individual bacterias present individually or in formulation (VF).

TABLE 10

| Glucose (%) Carbon source | Peptone (%) Nitrogen source | Yeast Extract (%) Growth factor | $KH_2PO_4$ (mg/100 mL) | $MgSO_4$ (mg/100 mL) |
|---|---|---|---|---|
| 2 | 0.5 | 0.5 | 5 | 1 |

Table 10 provides Medium for growth of *Bacillus subtilis* and *Bacillus coagulans*.

TABLE 11

| pH profile | pH at $6^{th}$ Hr |
|---|---|
| BS | 5.77 (initial pH 6) |
| BC | 6.14 (initial pH 6) |
| VF | 5.20 (initial pH 6) |
| BS | 5.31 (initial pH 8) |
| BC | 7.05 (initial pH 8) |
| VF | 5.28 (initial pH 8) |
| BS | 6.00 (initial pH 10) |
| BC | 6.82 (initial pH 10) |
| VF | 5.66 (initial pH 10) |

Table 11 shows Change in pH after 6 hours of the medium from initial pH >6 (pH 6, 8 and 10 respectively) post inoculation of BS and BC in comparison with the Vaginal Formulation (VF).

From the above table 11, it is shown that both BC and BS individually can bring down the pH to acidic, by producing lactic acid while they grow in-vitro or in-vivo. However, the drop in pH is always more (in all the cases from pH 6, 8 and 10) for the vaginal formulation (VF) as compared to the BS and BC.

Furthermore, comparative growth profile of the individual bacteria (BS and BC) in comparison with corresponding vaginal formulation at specific pH 7 and pH 8 up to 24 hours is also provided below (Table 12 and 13).

The following Tables 12 and 13 show Growth profileS (OD at 600 nm) at pH 7.0 and pH 8.0, respectively.

TABLE 12

| At pH 7.0 | | | | | | |
|---|---|---|---|---|---|---|
| Time (Hr) | BS | Only BS with GA, CA | BC | Only BC with GA, CA | BS + BC Without GA and CA | BS + BC with GA, CA |
| 3 | 0.028 | 0.074 | 0.022 | 0.032 | 0.073 | 0.089 |
| 6 | 0.107 | 0.119 | 0.073 | 0.103 | 0.136 | 0.165 |
| 9 | 0.134 | 0.150 | 0.099 | 0.143 | 0.167 | 0.210 |
| 12 | 0.150 | 0.248 | 0.108 | 0.176 | 0.174 | 0.278 |
| 15 | 0.182 | 0.260 | 0.168 | 0.198 | 0.245 | 0.384 |
| 18 | 0.226 | 0.336 | 0.338 | 0.476 | 0.447 | 0.521 |
| 21 | 0.295 | 0.375 | 0.458 | 0.587 | 0.643 | 0.701 |
| 24 | 0.398 | 0.479 | 0.621 | 0.663 | 0.792 | 0.915 |

Table 12 above shows Growth profile at pH 7 (CA is Citric Acid & GA is Gallic Acid).

From the above Table 12, it is evident that the growth is higher in case of combined formulation (BS+BC+CA+GA) as against only *Bacillus subtilis*, or only *Bacillus coagulans* or each present with citric acid and gallic acid at the end of 24 hours starting from initial pH of 7.

TABLE 13

| At pH 8.0 | | | | | | |
|---|---|---|---|---|---|---|
| Time (Hr) | BS | BS with GA, CA | BC | BC with GA, CA | BS + BC Without GA, CA | BS + BC with GA, CA |
| 3 | 0.073 | 0.086 | 0.0543 | 0.054 | 0.055 | 0.058 |
| 6 | 0.092 | 0.118 | 0.072 | 0.097 | 0.083 | 0.119 |
| 9 | 0.114 | 0.122 | 0.102 | 0.155 | 0.166 | 0.176 |
| 12 | 0.195 | 0.162 | 0.122 | 0.188 | 0.168 | 0.199 |
| 15 | 0.260 | 0.205 | 0.139 | 0.207 | 0.225 | 0.249 |
| 18 | 0.281 | 0.268 | 0.243 | 0.384 | 0.289 | 0.359 |
| 21 | 0.318 | 0.357 | 0.323 | 0.404 | 0.485 | 0.562 |
| 24 | 0.414 | 0.564 | 0.399 | 0.441 | 0.594 | 0.760 |

Table 13 shows Growth profile at pH 8 (CA is Citric Acid & GA is Gallic Acid).

From the above Table 13, it is evident that the growth is higher in case of combined formulation (BS+BC+CA+GA) as against only *Bacillus subtilis*, or only *Bacillus coagulans* or each present with citric acid and gallic acid at the end of 24 hours starting from initial pH of 8.

Example 5

Growth of inherent vaginal bacteria (Doderlein Bacteria) in presence of *Bacillus coagulans.*

To show the enhanced growth of doderlein vaginal bacteria (for example *Lactobacillus* gasseri and *Lactobacillus acidophilus*) in presence of BS+BC (as they are present in the present vaginal formulation) it is shown that the growth of doderlein bacteria (i.e. *Lactobacillus* gasseri and *Lactobacillus acidophilus*) is higher as compared when they are grown individually without the presence of *Bacillus coagulans* and *Bacillus subtilis*, thereby completely eliminating the possibilities of recurrence of infections by the pathogens due to increased growth of the inherent doderlein bacteria.

TABLE 14

| | Growth Profile (CFU/100 ml) after 24 hours | |
|---|---|---|
| Organism | Without BS + BC | With BS + BC |
| *Lactobacillus gaseri* (initial concentration 07 × $10^8$ CFU/100 ml) | 30 × $10^8$ pH 4.36 | 39 × $10^8$ pH 4.34 |
| *Lactobacillus acidophilus* (initial concentration 07 × $10^8$ CFU/100 ml) | 15 × $10^8$ pH 4.66 | 21 × $10^8$ pH 4.74 |

Table 14 shows Comparative growth of *Lactobacillus* gasseri and *Lactobacillus acidophilus* in presence of combination of *Bacillus subtilis* and *Bacillus coagulans.*

The above table 14 concludes that, (i) at least 30% increase in growth of *Lactobacillus* gasseri is seen when present in proximate with vaginal formulation than only presence of *Lactobacillus* gasseri. (ii) at least 40% increase in growth of *Lactobacillus acidophilus* is seen when present in proximate with vaginal formulation than only presence of *Lactobacillus acidophilus.*

Example 6

Formulations and Stability

Following formulations have been prepared to taste the stability in terms of potency of the spores of *Bacillus coagulans* and *Bacillus subtilis* for a period of at least 6 months at 40° C.

TABLE 15

| Formulation 1 along with excipients | |
|---|---|
| Formulation 1 | Potency |
| *B coagulans* | 1 Billion |
| *B subtilis* | 1 Billion |
| Citric acid | 15 mg |
| Gallic acid | 40 mg |
| Carbopol | q.s |
| Carboxymethyl cellulose | q.s |
| Polycarboxylic acid | q.s |
| Lactose | q.s |
| Boric acid | q.s |

TABLE 16

| Formulation 1 | Potency | Initial | 3 Months | 6 Months |
|---|---|---|---|---|
| *B coagulans* | $1 \times 10^9$ | 1029 msg* | 1017 msg | 1008 msg |
| *B subtilis* | $1 \times 10^9$ | 1045 msg | 1028 msg | 1013 msg |

*msg: million spores per gram

Table 16 shows Stability of Formulation 1 in terms of potency of *Bacillus coagulans* and *Bacillus subtilits* at 40° C.

TABLE 17

| Formulation 2 along with excipients | |
|---|---|
| Formulation 2 | Potency |
| *B coagulans* | 1 Billion |
| *B subtilis* | 1 Billion |
| Citric acid | 20 mg |
| Gallic acid | 20 mg |
| Polycarbophill | q.s |
| Beta Cyclodextrin | q.s |
| Sodium bicarbonate | q.s |
| Adipic acid | q.s |
| Boric Acid | q.s. |

TABLE 18

| Formulation 2 | Potency | Initial | 3 Months | 6 Months |
|---|---|---|---|---|
| *B coagulans* | $1 \times 10^9$ | 1023 msg* | 1008 msg | 1012 msg |
| *B subtilis* | $1 \times 10^9$ | 1056 msg | 1027 msg | 1007 msg |

*msg: million spores per gram

Table 18 shows Stability of Formulation 2 in terms of potency of *Bacillus coagulans* and *Bacillus subtilits* at 40° C.

The results show that there is little or minimum loss of potency of the *Bacillus coagulans* and *Bacillus subtilis* for a span of 6 months at 40° C. Therefore it is concluded that the formulations comprising *Bacillus coagulans, Bacillus subtilis*, citric acid, gallic acid in combination with other excipients are stable and therefore is stable for a period of at least 2 years without the need of any cold chain storage requirements.

It may also be noted that the excipients as shown are non-exhaustive in nature. The invention includes in its scope additional formulations that may be potentially developed by adding other excipients as per the need and mode of application of the formulation. Mere replacement of excipients or addition of additional components in addition to *Bacillus coagulans, Bacillus subtilis*, citric acid, gallic acid, including a combination thereof is to be construed to be within the legitimate ambit and scope of the present invention.

Example 7

Mechanism of Action of the Probiotic Formulation of the Present Invention.

A healthy vagina is normally acidic with pH 3-4. When Bacterial vaginosis occurs, it is caused due to a mixed pathogenic and fungal infections. These pathogens and fungi colonize the vagina and do so by turning the environment from acidic to alkaline (pH >7). This shift to alkalinity strongly favors the pathogenic and fungal species and seriously impairs colonization by healthy bacteria (particularly beneficial lactobacilli species prevalent in the human vagina). The composition as presented in the form of the above mentioned formulations in Example 3 are all designed to disrupt and kill pathogenic fungal and bacterial strains which is already established, further shift of pH to acidic encourage recolonization by healthy vaginal flora. After the formulation is brought in contact with the vaginal environment, the acidifiers particularly the citric acid and gallic acid begin their action by reducing the pH from greater than 7 (in case of infected vagina). Further, citric acid and gallic acid along with the available moisture content inside vaginal environment induces conversion of the spores of *Bacillus coagulans* and *Bacillus subtilis* to germinate as well, and the said probiotic bacterias start growing inside the vagina. Once the pH begins reaching less than 5-6, the bacterial strains begin germination. As a part of these, cell metabolism *Bacillus coagulans* and *Bacillus subtilis* secrete bacteriocins, lactic acid, short chain fatty acids, anti-fungal compounds and nutrient factors. These bacterial strains (including metabolites produced by the strains on site) in combination with the Gallic acid provide broad spectrum action against the infection causing organisms. Thus the site is now cleared for the return of normal vaginal flora. *Bacillus coagulans* and *Bacillus subtilis* both will not permanently colonize the vagina but will act as transient colonizers. However, during this transient period, these probiotic's metabolites will also promote growth of *Lactobacillus acidophilus* and *Lactobacillus* gasseri (native to a healthy vagina also called Doderlein bacteria). This leads to restoration of normal healthy vaginal flora and also the risk of recurrence of pathogenic infections in the vagina is severely reduced because the present composition promotes growth of dederlein bacteria or the native vaginal bacteria.

As compared with traditional antibiotic treatment, the step of restoring the healthy vaginal flora is completely ignored since antibiotics kill all good and bad bacteria thereby making room for the pathogens to invade again before the inherent native doderlein bacteria starts colonizing the vagina.

Additionally, the colonization of *Bacillus coagulans* and *Bacillus subtilis* is only temporary. Both *Bacillus coagulans* and *Bacillus subtilis* produce lactic acid. Production of lactic acid encourages replenishment and growth of native *Lactobacillus* species within the vagina which is inherent bacteria of the vagina. Therefore, the present composition automatically supplements the specific inherent bacteria which was originally present in the vagina of the specific subject. Thus, the present composition helps in the re-colonization of specific doderlein bacteria and not some other external probiotic as available according to the present state of the art. Due to the continuous availability of lactic acid, *Bacillus*

*coagulans* and the *Bacillus subtilis* slowly are outnumbered by doderlein lactic acid bacteria of the *Lactobacillus* species.

Therefore, without intending to be bound by any theory, the sequence of action may be summarized as follows: (1) Activate therapy via acidification of vagina due to the presence of citric acid and gallic acid; (2) Competitively inhibit and eliminate causative fungi and pathogens due to the bacteriocins released by BC and BS; and (3) Promote restoration of natural flora to prevent recurrence.

Advantages of the Invention

Additionally, the present invention as disclosed in the above formulations comprising of *Bacillus coagulans, Bacillus subtilis*, citric acid and gallic acid could check all different types of bacterial and fungal pathogens infecting the vagina. Hence the necessity for specific diagnosis is no more essential to be performed thereby saving the cost and time of treatment.

Application of the probiotic compositions of the present invention does not need any separate administration of antibiotics for treatment of pathogenic infections of the vagina. Thus it restricts development of antimicrobial resistance among the pathogens.

The combination of *Bacillus subtilis* and *Bacillus coagulans* in the present formulation is in the form of spores also containing citric acid and gallic acid compressed and converted into a tablet unlike all existing vaginal probiotic formulations which contain *Lactobacillus* strains in a vegetative form. Vegetative forms of the bacteria cannot sustain the high amount of pressure and load in the tablet formulation and therefore they are not stable, and their capacity to induce the desirable effect when administered in the vagina is highly compromised. These formulations also have a very short shelf life, and therefore require cold chain transportation. Contrarily the present invention is the form of spores and hence they are more stable and has a better shelf life without the need of any cold chain transportation.

The present probiotic formulations intended for direct vaginal administration germinates within the vagina as soon as they get the required moisture content post administration. The citric acid and gallic acid content in the formulation acts as synergistic initiators for effective germination of the spores. As explained earlier, these two bacilllus species i.e. *B. subtilis* and *B. coagulans* acts as an in-situ producer of lactic acid, thereby allows the doderlein *Lactobacillus* species to replenish and grow exponentially. Further, with passage of time, the count of *B. subtilis* and *B. Coagulans* species reduces automatically with the growth of doderlein *Lactobacillus* bacteria as these two *bacillus* species are not the natural inhabitants of the vaginal microbial ecosystem. Therefore, this combined probiotic formulation encourages the competitive inhibition of pathogens and restoration of natural microbial ecological balance of the human vagina.

Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entireties for all purposes.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

We claim:

1. A composition for competitive inhibition of vaginal pathogens in a human subject comprising *Bacillus coagulans* SNZ 1969*, Bacillus subtilis* SNZ 1972, citric acid and gallic acid, wherein said *Bacillus coagulans* is present at a concentration between 550 million to 700 million colony forming units (cfu), *Bacillus subtilis* is present at a concentration between 25 million to 125 million cfu, citric acid between 10 mg to 20 mg and said gallic acid between 60 mg to 100 mg per unit dose, wherein said citric acid and said gallic acid in the composition initially acidifies the internal vaginal environment to promote germination of said *Bacillus coagulans* and said *Bacillus subtilis* in said composition thereby facilitating competitive inhibition of pathogens, and wherein said composition is provided in a gel, ointment, cream, tablet, capsule, pessary, foam, wash, tampon, applicator, pad, or suppository.

2. The composition of claim 1, wherein said composition is for competitive inhibition of pathogens against but not limited to bacterial vaginosis, aerobic vaginitis, vaginal yeast and fungal pathogenic infections without the need of prior diagnosis thereof and restoration of doderlein vaginal microbial ecological balance.

3. A composition for competitive inhibition of vaginal pathogens in a human subject comprising *Bacillus coagulans* SNZ 1969*, Bacillus subtilis* SNZ 1972, citric acid and gallic acid, wherein said *Bacillus coagulans* is present at a concentration between 25 million to 125 million colony forming units (cfu), *Bacillus subtilis* is present at a concentration between 550 million to 700 million cfu, citric acid between 60 mg to 100 mg and said gallic acid between 10 mg to 20 mg per unit dose, wherein said citric acid and said gallic acid in the composition initially acidifies the internal vaginal environment to promote germination of said *Bacillus coagu-*

*lans* and said *Bacillus subtilis* in said composition thereby facilitating competitive inhibition of pathogens, and wherein said composition is provided in a gel, ointment, cream, tablet, capsule, pessary, foam wash, tampon, applicator, pad, or suppository.

4. A method of competitive inhibition of pathogens and restoration of inherent doderlein bacteria without administering any *Lactobacillus* bacteria from external sources thereby maintaining microbial ecological balance of the reproductive and genital organs, particularly the vagina, for treatment of bacterial vaginosis, aerobic vaginitis, vaginal yeast and fungal pathogenic infections without the need of prior diagnosis thereof comprising the step of administering the composition of claim 1 comprising *Bacillus coagulans* SNZ 1969*, Bacillus subtilis* SNZ 1972, citric acid, and gallic acid, wherein said *Bacillus coagulans* and *Bacillus subtilis* are present in the form of spores.

5. A method for reduction of recurrence of pathogenic infections comprising the step of administering the composition of claim 1 comprising *Bacillus coagulans* SNZ 1969*, Bacillus subtilis* SNZ 1972, citric acid, and gallic acid, wherein the growth of doderlein *Lactobacillus* bacteria without the presence of *Bacillus coagulans* and *Bacillus subtilis* is more than the growth of doderlein *Lactobacillus* bacteria without the presence of *Bacillus coagulans* and *Bacillus subtilis*.

* * * * *

UNITED STATES PATENT AND TRADEMARK OFFICE

CERTIFICATE OF CORRECTION

PATENT NO. : 12,097,225 B2
APPLICATION NO. : 16/788990
DATED : September 24, 2024
INVENTOR(S) : Raunak Jay Soman et al.

It is certified that error appears in the above-identified patent and that said Letters Patent is hereby corrected as shown below:

In the Claims

In Claim 5, Column 23, Line 25, replace the term "without" with the term --in--.

In Claim 5, Column 23, Line 25, add the term "said" before each instance of the term "Bacillus".

In Claim 5, Column 23, Line 27, add the term "said" before the term "Bacillus".

In Claim 5, Column 23, Line 28, add the term "said" before the term "Bacillus".

Signed and Sealed this
Twenty-sixth Day of November, 2024

Katherine Kelly Vidal

Katherine Kelly Vidal
*Director of the United States Patent and Trademark Office*